United States Patent [19]

Klein et al.

[11] Patent Number: 4,835,239

[45] Date of Patent: May 30, 1989

[54] DIISOCYANATES AND THEIR USE FOR THE PREPARATION OF POLYURETHANES

[75] Inventors: Gerhard Klein, Monheim; Dieter Arlt, Cologne, both of Fed. Rep. of Germany

[73] Assignee: Bayer Aktiengesellschaft, Leverkusen, Fed. Rep. of Germany

[21] Appl. No.: 879,756

[22] Filed: Jun. 27, 1986

Related U.S. Application Data

[62] Division of Ser. No. 691,103, Jan. 14, 1985, Pat. No. 4,613,685.

[30] Foreign Application Priority Data

Jan. 26, 1984 [DE] Fed. Rep. of Germany ....... 3402623

[51] Int. Cl.[4] ..................... C08G 18/00; C08G 18/81
[52] U.S. Cl. ...................................... 528/44; 528/45; 528/85
[58] Field of Search ...................... 528/44, 45

[56] References Cited

U.S. PATENT DOCUMENTS

| | | | |
|---|---|---|---|
| 2,692,275 | 10/1954 | Bortnick | 260/453 A |
| 3,352,830 | 11/1967 | Schmitt et al. | 260/453 A X |
| 3,799,965 | 3/1974 | MacKay et al. | 260/453 A |
| 3,904,665 | 9/1975 | Decot et al. | 260/453 A |
| 4,505,860 | 3/1985 | Klein et al. | 260/453 A |

FOREIGN PATENT DOCUMENTS 1022222 1/1954 Fed. Rep. of Germany.
253222 3/1967 Switzerland.

OTHER PUBLICATIONS

Mark, J. E. and Odian, G., *Polymer Chemistry*, ACS Short Courses, by American Chemical Society, pp. 104–107.

*Primary Examiner*—John Kight
*Assistant Examiner*—Dennis R. Daley
*Attorney, Agent, or Firm*—Gene Harsh; Joseph C. Gil; Thomas W. Roy

[57] ABSTRACT

The present invention relates to diisocyanates having an isocyanate content of from about 20 to 50% by weight, optionally in the form of isomeric mixtures, characterized in that, in addition to containing a sterically unhindered isocyanate group attached to a primary aliphatic carbon atom, they contain a sterically hindered isocyanate group attached to a tertiary carbon atom which forms part of a cycloaliphatic ring system.

The invention also relates to the use of the new diisocyanates, optionally blocked with blocking agents for isocyanate groups, as isocyanate component for the preparation of polyurethanes suitable for use as coatings.

14 Claims, No Drawings

DIISOCYANATES AND THEIR USE FOR THE PREPARATION OF POLYURETHANES

This application is a division of application Ser. No. 691,103 filed Jan. 14, 1983 now U.S. Pat. No. 4,613,685.

BACKGROUND OF THE INVENTION

1. Field of the Invention

This invention relates to new aliphatic-cycloaliphatic diisocyanates containign a sterically hindered, cycloaliphatically bound isocyanate group in addition to a sterically unhindered, aliphatically bound isocyanate group, and to the use of the new diisocyanates as starting material for the preparation of polyurethanes.

2. Description of the Prior Art

The diisocyanates with aliphatically and/or cycloaliphatically bound isocyanate groups used in industrial polyurethane chemistry, e.g. 1-isocyanato-3,3,5-trimethyl-5-isocyanatomethyl -cyclohexane (isophorone diisocyanate), 4,4'-diiosocyanato -dicyclohexylmethane or hexamethylene diisocyanate, are eminently suitable for the preparation of light-fast polyurethanes on account of their aliphatic character. These diisocyanates are therefore used in particular for the production of polyurethane lacquers or the production of lacquer polyisocyanates. One disadvantage of these important aliphatic and/or cycloaliphatic diisocyanates known in the art is to be seen in the fact that their isocyanate groups are identical or similar in their reactivity towards compounds containing isocyanate reactive groups. This gives rise to difficulties, for example, in reactions in which only one isocyanate group is intended to undergo reaction, e.g. in the preparation of isocyanate prepolymers by the reaction of one isocyanate group of the diisocyanate with hydroxyl groups of polydroxyl compounds of the type used in polyurethane chemistry.

It was therefore an object of the present invention to provide new aliphatic-cycloaliphatic diisocyanates in which the isocyanate groups should differ so distinctly in their reactivity as to enable isocyanate prepolymers having free isocyanate groups to be prepared without chain lengthening reactions occuring to any significant extent.

This problem was able to be solved by the preparation of the new diisocyanates according to this invention.

SUMMARY OF THE INVENTION

The present invention relates to diisocyanates having an isocyante content of from about 20 to 50% by weight, optionally in the form of isomeric mixtures, characitrized in that, in addition to containing a sterically unhindered isocyante group attached to a primary aliphatic carbon atom, they contain a sterically hindered isocyanate group attached to a tertiary carbon atom which forms part of a cycloaliphatic ring system.

The invention also relates to the use of the new diisocyanates, optionally blocked with blocking agents for isocyanate groups, as isocyanate component for the preparation of polyurethanes.

DETAILED DESCRIPTION OF THE INVENTION

Preferred diisocyanates according to this invention correspond to the formula

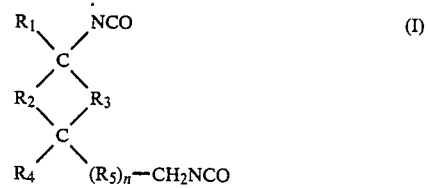

in which $R_1$ represent an alkaly group having 1 to 4 carbon atoms, preferably a metyl group, $R_2$ and $R_3$, which may be identical or different, each represent a divalent, linear or branched chain, saturated hydrocarbon group having 1 to 4, preferably 1 to 3 carbon atoms, the sum of the carbon atoms of these groups preferably being from 3 to 6, in particular 3 or 4.

$R_4$ represents hydrogen or an alkyl group having 1 to 4 carbon atoms, preferably hydrogen of a methyl group, $R_5$ represents a divalent, linear or branched chain, saturated, aliphatic hydrocarbon group having 1 to 4 carbon atoms, and n represents 0 or 1.

Particularly preferred diisocyanates according to the invention are, for example, 1-isocyanato-1-methyl-4(3)-isocyanatomethylcyclohexane, which is generally present as a mixture of the 4- and 3-cyanatomethyl isomers, 1-isocyanato-1-methyl-4-(4-isocyanatobut-2yl)-cyclohexane or 1-isocyanato-1, 2,2-trimethyl-3-(2-isocyanatoethyl)-cyclopentane.

The diisocyanates according to the invention may be prepared, for example, by reacting unsaturated amines corresponding to the general formula II

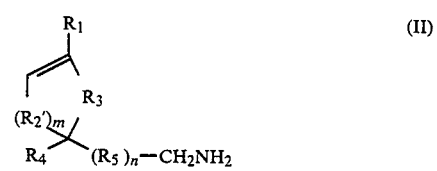

wherein $R_2'$ represents a divalent, satured, linear or branched chain hydrocarbon group having 1 to 3 carbon atoms, m represents 0 or 1, and $R_1$, $R_3$, $R_4$, $R_5$ and n have the meaning indicated above or amino alcohols corresponding to the general formula III

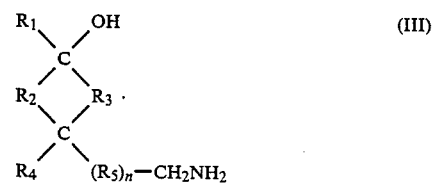

in which $R_1$, $R_2$, $R_3$, $R_4$, $R_5$ and n have the meaning indicated above, with hydrocyanic acid in a Ritter reaction to form the diamines coresponding to the general formula IV

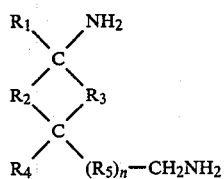  (IV)

The diisocyanates of the general formula I are obtained from the diamines of the general formula IV by phosgenation.

The unsaturated amines corresponding to the general formula II are either known or obtainable by catalytic hydrogenation from compounds corresponding to the general formula V

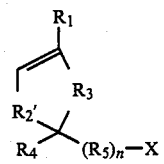  (V)

in which
X represents —CHO or —CN and
$R_1$, $R_2$, $R_3$, $R_4$, $R_5$ and n have the meaning already indicated above.

The basic substances corresponding to the general formula V may be obtained, for example, by the known Diels-Adler reaction from the corresponding bis-olefins having conjugated double bonds and unsaturated nitriles or aldehydes or by hydrofomylation from the corresponding unsaturated hydrocarbons. Thus, for example, the Diels-Alder adduct of formulae VIa and VIb

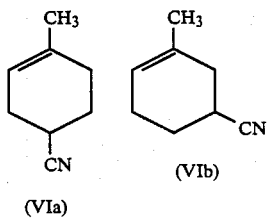

present as a mixture of position isomers is the basic substance of 1-isocyanato-1-methyl-4(3)-isocyanato-methyl cyclohexane, which is also present as a mixture of position isomers, while the compoud corresponding to the forumula VII

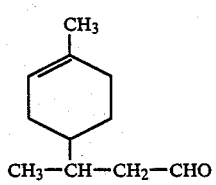  (VII)

obtainable by the hydroformylation of limonene is the basic substance of 1-isocyanato-1-methyl4(4-isocyanatobut-2yl)-cyclohexane. The basic substance of 1-isocyanato-1,2,2-trimethyl3-(2-isocyanatoethyl)-cyclopentane is campholene aldehyde corresponding to formula VIII

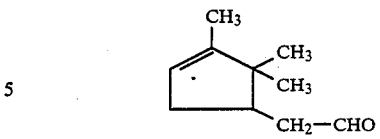  (VIII)

Other basic substances corresponding to the general formula V may be prepared analogously by suitable choice of the staring materials used for their preparation. Compounds VI to VIII are known in the literature (VI: Chem. Abstr. 71, 112475 F; VII: EP-A-0008459; VIII: Berichte 68B 1430 (1935)).

The Ritter reaction of the unsaturated amines corresponding to the general formula II or of the amino alcohols corresponding to the general formula III is carried out in the presence of a strong acid such as sulphuric acid, phosphoric acid, alkyl or aryl sulphonic acids or trifluoroacetic acid. Sulphuric acid is preferred. The water content of the acid may vary from about 5 to 50%, but is preferably from about 25 to 35%. The quantity of acid used per mol of unsaturated amine is from about 1 to 3 mol, preferably about 2 mol. Based on the unsaturated amine corresponding to the general formula II or to the amino alcohol corresponding to the general formula III, an equimolar quantity of an excess of up to 1 mol of hydrocyanic acid is used. According to a preferred procedure, the unsaturated amine corresponding to the general formula II is added to the acid, and the hydrocyanic acid id added subsequently. The temperature is maintained in the region of about 0° to 25° C. during addition of the amine and from about 10° to 50° C., preferably from about 30° to 45° C. during the addition of hydrocyanic acid. After a reaction time of about 2 to 10 hours, preferably about 4 to 6 hours, the formamide formed is subjected to acid hydrolysis and the diamines of the general formula IV formed in the reaction is released by neutralization with a base, e.g. sodium hydroxide solution.

The diamine of the general formula IV obtained by the Ritter reaction is phosgenated in known manner. For this purpose, the diamine may, for example, be saturated with carbon dioxide in an inert solvent at temperatures in the region of from about 0° to 150° C., preferably from about 80° to 100° C. The resulting addition product is then reacted with phosgene at about 0° to 200° C., preferably at about 120° C., to 150° C., form the diisocyanate corresponding to the general formula I. Any inert solvents having a boiling point which is sufficiently high for phosgenation and sufficiently different from that of the diisocyanate may be used. Chlorobenzenes, nitrobenzenes, xylenes, Tetralin solvent (1,2,3,4-tetrahydronaphthalene) and Decalin solvent (decahydronaphthalene) are preferred.

According to another method of phosgenation, the diamine is added in an inert solvent to a solution of phosgene in the same solvent at temperatures in the range of from about -20° C. to 50° C. The excess of phosgene over the amine should amount to about 2 to 10 mol, preferably about 4 to 6 mol. Further reaction of the addition product to form the diisocyanate is then carried out at a temperature of from about 20° to 200° C., preferably from about 120° to 150° C., The diisocyanates according to the invention obtained by this procedure have an isocyanate content of from about 20 to 50, by weight, preferably from about 30 to 48% by weight, and generally consist of stereoisomeric mixtures, a although the diisocyanates according to the invention may also consist of mixtures of position isomers, particularly when unsaturated nitriles corresponding to the general formula V obtained by the Diels-Alder reaction are used as basic substance.

The diisocyanates according to this invention corresponding to the general formula I are valuable starting materials for the ppreparation of polyisocyanate polyaddition products, preferably polyurethanes. These products are prepared by reacting the diisocyanates according to the present invention with compounds containing isocyanate-reactive groups, preferably at least a portion of these compounds containing hydroxyl groups, by the isocyanate polyaddition process. For this purpose, the diisocyanates may be used either an such or blocked with blocking agents for isocyanate groups, such as -caprolactam, methal-ethyl ketoxime, diethyl malonate or ethyl acetoacetate. The new diisocyanates are suitable in particular for the preparation of polyurthanes by the two-stage process in which prepolymers having free isocyanate groups are produced in a first stage from the diisocyanates according to the inventin and sub-equivalent quantities of organic polyhydroxyl compounds of the type known in polyurethane chemistry, and these prepolymers are then converted in a seconde reaction stage into the high molecular weight polyurethane by means of suitable chain lengthening agents. All the processes mentioned for the preparation of polyurethanes using diisocyanates according to this invention are applicable in particular to the lacquer sector, i.e. for the production of one-component and two-component polyurethane lacquers.

The percentages given in the following Examples are percentages by weight. All indications of pressure given with the boiling points are in mbar.

Examples

The following unsaturated amines are used in the examples which follow:

Unsaturated Amine A:

605 g of 4(5)-Cyano-1-methylcyclohexane were dissolved in 500 ml of liquid ammonia in a stirrer autoclave and hydrogenated under a hydrogen pressure of 100 bar over 40 g of Raney nickel iron at 90° C. After evaporation of the ammonia, the product was filtered from the catalyst and distilled under vacuum. 550 g (88%) of 4(5)-amino-methyl-methylcyclohexene, bp.$_{10}$ 78°–80° C. were obtained. The proportions by weight of the 4-and 5-isomers was approximately 80:20.

Unsaturatede Amine B:

830 g of 3-(1-methylcyclohexen-4-yl)-butyr-aldehyde were dissolved in 800 ml of liquid ammonia in stirrer autoclave and hydrogenated under a hydrogen pressure of 100 bar over 50 g of Raney nickel iron at 90° C. After evaporation of the solvent, the product was filtered from the catalyst and distilled under vacuum. 720 g (86%) of 3-(1methylcyclohexen-4-yl)-butylamine, bp.$_{10}$ 120° C., were obtained.

Unsaturated Amine C:

620 g of Campholene aldehyde were dissolved in 600 ml of liquid ammonia in a stirrer autoclave and hydrogenated under a hydrogen pressure of 100 bar 50 g of Raney nickel iron at 90° C. After evaporation of the ammonia, the product was filtered from the catalyst and distilled under vacuum. 500 g (88%) of 4-Aminoethyl-1,5,5-trimethyl-cyclopentene, bp.$_{10}$ 85°–90° C., were obtained.

EXAMPLE 1

(a) Preparation of 1-amino-1methyl-4(3)-aminomethyl cyclohexane 1125 g of unsaturated amine A were added dropwise to 2650 g of 70% sulphuric acid at 10° to 25° C. and then 360 ml of hydrocyanic acid were added dropwise at 40° to 45° C. The reaction mixture was then stirred for 4 hours at 45° C., unreacted hydrocyanic acid was distilled off under vacuum and 2 liters of water were added. The reaction mixture was heated under reflux for 3 hours and made alkaline with 2.7 liters of 45% sodium hydroxide solution. The liquid was decanted from the salt which has precipitated, the organic phase was separated off, the salt and aqueous phase were washed twice with toluene, and the product was distilled under vacuum over an 80 cm column. 907 g of 1-Amino-1-methyl-4(3)-aminomethylcyclohexamne, bp.$_{10}$ 95°–105° C., and 172 g of 4(3)-aminomethyl-1-methyl-cyclohexanol, bp.$_{10}$ 115°–120° C., were obtained.

(b) Preparation of 1-amino-1-methyl-4(3)-amino-methyl-cyclohexane 175 g of 70% sulphuric acid were added dropwise at 20° to 30° C. to 71.5 g of 4(3)-aminomethyl-1-methylcyclohexanol (a by-product of the preparation of the diamine according to 1 (a)). 27 ml of hydrocyanic acid were added dropwise at 40° C. and the reaction mixture was then stirred for 4 hours at 45° C. Unreacted hydrocyanic acid was distilled off under vacuum and 100 ml of water were added. The reaction mixture was then heated under reflux for 3 hours, made alkaline with 200 ml of 45% sodium hydroxide solution and decanted to remove precipitated salt. the organic phase was separated off, the salt and aqueous phase were washed twice with toluene and the product was distilled under vacuum. 53 g of 1-Amino-1-methyl-4(3)-aminomehtylcyclohexane, bp.$_{10}$ 95°–105° C., were obtained.

(c) Preparation of 1-isocyanato-1-methyl-4(3)-isoxyanato-methylcyclohexane (1st method of phosgenation)

A solution of 71 g of 1-amino-1-methyl4(3)-aminomethylcyclohexane in 150 ml of dichlorobenzene was added dropwise at 0° C. to a solution of 250 g of phosgene in 350 ml of dichlorobenzene. The reaction mixture was heated to 150° C. in the course of 2 hours while phosgene was passed through. Phosgene continued to be introduced for 7 hours at 150° C. The phosgene was then expelled with nitrogen, the solvent was distilled off under vacuum and the residue was fractionated under vacuum. 73 g of 1-isocyanato-1-methyl-4(3)-isocyanatomethylcyclohexane, bp.$_{0.1}$ 95°–103° C., were obtained. Proportions by weight of 4- and 3-isomers approximately 80:20.

(d) Preparation of 1-isocyanato-1-methyl-4(3)-isocyanato-methyl cyclohexane (2nd method of phosgenation)

A solution of 71 g of 1-amino-1-methyl-4(3)- aminomethylcyclohexane in 1 liter of dichlorobenzene was saturated with $CO_2$ at 90° C. and stirred for 6 hours at 90° C. 100 g of phosgene were incorporated by condensation at 0° C. in the course of 2 hours while phosgene was passed through. The introductin of phosgene was continued for 10 hours at 150° C. and the residue of phosgene was then expelled with nitrogen, the solvent is distilled off under vacuum. The residue was fractionated under vacuum. 71 g of 1-Isocyanato-1-methyl-4(3)-isocyanato methylcyclohexane, bp.$_{0.1}$ 95°–103° C., were obtained. Proportions by weight of the 4-and 3-isomers approximately 80:20.

EXAMPLE 2

(a) Preparation of 1-amino-1-methyl-4-(4-aminobut-2-yl)-cyclohexane 660 g of unsaturated amine B were added dropwise to 1200 g of 70% sulphuric acid at 5° to 10° C. 170 ml of hydrocyanic acid were added dropwise at 30°–35° C. and then the reaction mixture was then stirred for 4 hours at 45° C. and excess hydrocyanic acid was distilled off under vacuum. 300 ml of water were then added and the reaction mixture was heated under reflux for 3 hours, made alkaline with 1400 ml of 45% sodium hydroxide solution and decanted to separate it from the precipitated salt. The phases were separated, the salt and the aqueous phase were extracted twice with toluene, and the product was distilled under vacuum. 656 g (90%) of 1-amino-1-methyl-4-(4-amino-but-2-yl)-cyclohexane, bp.$_{10}$135°–137° C., were obtained.

(b) Preparation of 1-isocyanato-1-methyl-4(4-iso-cyanato-but-2-yl)-cyclohexane

A solution of 46 g of 1-amino-methyl-4-(4-aminobut-2-yl)-cyclohexane in 80 ml of dichloro-benzene was added dropwise at 0° C. to a solution of 125 g of phosgene in 200 ml of dichlorobenzene. The reaction mixture was heated to 150° C. in the course of 2 hours while phosgene was introduced. The introduction of phosgene was continued for a further 3 hours at 150° C. The residual phosgene was expelled with nitrogen, the solvent was distilled off under vacuum and the residue was fractionated under vacuum. 50 g (85%) of 1-isocyanato-1methyl-4-(4-isocyanatobut-2-yl)-cyclohexane, bp.$_{0.1}$130° C., were obtained.

EXAMPLE 3

(a) Preparation of 1-amino-1,2,2-trimethyl-3-(2-amino-ethyl)-cycopentane:

100 g of 80% sulphuric acid were added dropwise at 0° to 5° C. to 80 ml of hydrocyanic acid. 50 g of unsaturated amino C were then added at 5° to 10° C. and the reaction mixture was stirred for 4 hours at 45° C. and excess hydroxyanic aicd is distilled off. 80 ml of water were added and then the reaction mixture was heated under reflux for 3 hours, made alkaline with 200 g of 45% sodium hydroxide solution and decanted to separate it from the precipitated salt. The phases were separated, the salt and the aqueous phase were extracted twice with toluene and the product was distilled under vacuum. 40 g (72%) of 1-amino-1,2,2-trimethyl-3-(2-aminoethyl)-cyclopentane, bp.$_{10}$125° C., were obtained.

(b) Preparation of 1-isocyanato-1,2,2-trimethyl-3-(2-isocyanatoethyl)-cyclopentane A solution of 42.5 g of 1-amino-1,2,2-trimethyl-3-(2-aminoethyl)-cyclopentane in 80 ml of dichlorobenzene was added dropwise at 0° C. to a solution of 125 g of phosgene in 200 ml of dichlorobenzene. The reaction mixture was heated to 150° C. in 2 hours while phosgene was passed through. The introduction of phosgene was continued for a further 4 hours at 150° C. The residual phosgene was expelled with nitrogen, the solvent was distilled off under vacuum and the residue was fractionated under vacuum. 33 g (60%) of 1-isocyanato-1,2,2-trimethyl-3-(2-isocyanatoethyl)-cyclopentane, bp.$_{0.1}$120° C., were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a polyisocyanate polyaddition product which comprises reacting
(a) at least one diisocyanate or an isomeric mixture thereof having an isocyanate content of about 30 to 48% and corresponding to formula (I)

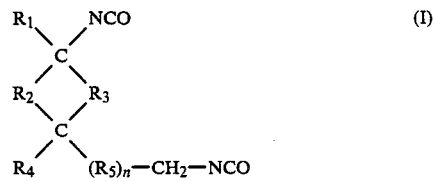

wherein
$R_1$ represents an alkyl group having from 1 to 4 carbon atoms, $R_2$ and $R_3$, which may be identical or different, represent linear or branched chain, divalent hydrocarbon groups having 1 to 4 carbon atoms,
$R_4$ represents hydroben or an alkyl group having 1 to 4 carbon atoms,
$R_5$ represents a linear or branched chain, saturated, divalent hydrocarbon group having 1 to 4 carbon atoms, and
n represents 0 or 1, with
(b) a compound containing isocyanate-reactive hydrogens.

2. The process of claim 1 wherein
$R_1$ represents a methyl group, $R_2$ and $R_3$ represent identical or different, linear divalent, saturated hydrocarbon groups having 1 to 3 carbon atoms, with the prviso that the sum of the number of carbon atoms of groups $R_2$ and $R_3$ amounts to 3 or 4, and
$R_4$ represents hydrogen or a methyl group.

3. The process of claim 1 wherein said diisocyuanate comprises 1-isocyanato-1methyl-4(3)-isocyanatomethyl -cyclo-hexane.

4. The process of claim 1 wherein said diisocyanate comprises 1-isocyanato-1-methyl-4-(4-isocyanatobut-2-yl)-cyclohexane.

5. The process of claim 1 wherein said diisocyanate comprises 1-isocyanato-1,2,2-trimethyl-3-(2-isocyanatoethyl)-cyclopentane.

6. The process of claim 1 wherein said polyisocyanate polyaddition product is a polyurethane and component (b) comprises a compound containing hydroxyl groups.

7. The process of claim 1 wherein said diisocyhanate is blocked with a blocking agent for isocyanate groups.

8. The process of claim 6 wherein said diisocyanate is blocked with a blocking agent for isocyanate groups.

9. The process of claim 3 wherein said polyiscyanate polyaddition product is a polyurethane and component (b) comprises a compound containing hydroxyl groups.

10. The process of claim 9 wherein said diisocyanate is blocked with a blocking agent for iscoyanate groups.

11. The polyisocyanate polyaddition product produced in accordance with claim 1.

12. The polyisocyanate polyaddition product produced in accordance with claim 3.

13. The polyisocyanate polyaddition product produced in accordance with claim 6.

14. The polyisocyanate polyaddition product produced in accordance with claim 9.

* * * * *